United States Patent [19]

Saad

[11] 4,027,068

[45] May 31, 1977

[54] USE OF CHITIN DERIVATIVES IN AUTOMOBILE PRODUCTS

[75] Inventor: Hosny Younes Saad, Ramsey, N.J.

[73] Assignee: American Cyanamid Company, Stamford, Conn.

[22] Filed: Sept. 12, 1975

[21] Appl. No.: 612,973

[52] U.S. Cl. ................................ 428/426; 106/13; 252/70; 427/165; 428/532; 428/905; 536/20
[51] Int. Cl.² ..................... B32B 17/06; C09K 3/18
[58] Field of Search .................. 428/426, 435, 532; 252/70; 106/13, 2; 536/20; 427/165

[56] References Cited

UNITED STATES PATENTS

| | | | |
|---|---|---|---|
| 2,416,051 | 2/1947 | Gilbert | 428/426 |
| 3,879,376 | 4/1975 | Vanlerberghe | 424/361 |

FOREIGN PATENTS OR APPLICATIONS

| | | | |
|---|---|---|---|
| 960,508 | 6/1964 | United Kingdom | 428/409 |

*Primary Examiner*—Ellis Robinson
*Attorney, Agent, or Firm*—Charles J. Fickey

[57] ABSTRACT

A method of using chitin derivatives as defoggers for clear surfaces and as deodorizers is disclosed.

6 Claims, No Drawings

USE OF CHITIN DERIVATIVES IN AUTOMOBILE PRODUCTS

This invention relates to a method of alleviating fog formation on clear surfaces, such as windshields and windows, while at the same time optionally releasing controlled levels of fragrance.

It is an object of the present invention to provide a material which can be applied to the clear surfaces in order to both control fog formation, and also provide a controlled release of fragrance.

According to the present invention, certain carboxyl containing chitin derivatives may be applied to windows or other clear surfaces as aids in reducing fogging and as carriers for a perfume. The chitin derivatives form a thin, clear film which acts to absorb water, while at the same time remaining clear. Thus when fog begins to condense on the surface, the water is absorbed by the film of the chitin derivative. Later, as the conditions change and condensation is no longer occurring, the film loses some of the moisture and is thus able to absorb a water condensate on a later occasion. The film of the chitin derivative also acts to retain perfume components, possibly because chitin contains polar groups which can interact with perfume components. For use in this invention, chitin derivatives should be soluble in mixtures of alcohol and water, and soluble in basic solutions, so that they may be dissolved readily in alcohol and water for application to the surface, and be removable by either basic detergent solutions, or by alcohol water solutions. However, such derivatives should not be readily soluble in water so that they do not dissolve when a fog forms on the surface.

Chitin itself is a naturally occurring poly-N-acetyl-glucosamine which can be isolated from several sources. A major source of chitin is the exoskeleton of anthropods, particularly those of crustaceans, such as shrimps. Chitin is available in several molecular weight ranges, but whatever the molecular weight, it is a hard, highly crystalline material, which is difficult to dissolve. Thus, chitin itself would not be suitable for use in the present invention. However, carboxyl containing derivatives do have the desired solubility properties in that they dissolve slowly in water, and dissolve readily in basic detergent solutions.

Derivatives of chitin can be formed by attaching a substituent to the 6 hydroxyl oxygen or by removing the N-acetyl group to form chitosan, and attaching another substituent to the nitrogen. Chitosan itself is commercially available, and is thus a useful starting material for preparation of chitin derivatives in which a substituent is attached to the nitrogen. The carboxy containing chitin derivatives which are useful in the present invention, are O-carboxy-alkyl chitins, in which a carboxy alkyl group is attached to the 6-hydroxyl oxygen through the alkyl group; N-carboxyalkyl chitosans in which a carboxyalkyl group is attached to the nitrogen through the alkyl groups, and N-carboxyacyl chitosan in which the nitrogen is acylated with a material which contains a free carboxyl group in addition to the acyl group which is attached to the nitrogen. The O-carboxyalkyl chitin may be prepared by reacting chitin, in an organic solvent, with a strong base such as an alkali metal hydroxide or alkali metal lower hydroxide and an alkyl halide containing a carboxyl group. The N-carboxyalkyl chitosans may be prepared by reacting chitosan with a halocarboxylic acid, in an organic solvent. The N-carboxyacyl chitosans may be prepared by reacting chitosan with a base and an anhydride of a di-acid, as disclosed in British Pat. No. 1,387,883.

Instead of the simple derivatives disclosed above, it is possible to prepare derivatives which have more than one type of substituent on the chitin chain. These other substituents need not be limited to carboxy containing substituents, and in fact, alkyl and substituted alkyl substituents are often preferred because they can modify the solubility of the chitin derivative. Thus, if a chitin derivative which has only substituents containing carboxyl groups is too soluble in water for the given use, a less soluble derivative may be prepared by replacing some of the carboxyl containing substituents with alkyl or substituted alkyl substituents. The alkyl substituents tend to make the chitin derivative soluble in organic solvents rather than in water. Thus, it is possible to achieve any desired degree of water or organic solvent solubility. Since the carboxyl groups still attract water, films of carboxyl containing chitin derivatives will be hygroscopic even if the derivative is only marginally soluble in water. Of course, owing to the reactivity of the carboxyl groups even a derivative which is only marginally soluble in water will be soluble in a basic detergent solution.

As noted above, alkyl or substituted alkyl groups can be used to replace the carboxyl containing substituents in order to modify the solubility of the chitin derivative. Example of the substituents which may be attached to the alkyl groups are alkoxy and carboalkoxy. Generally, the chitin derivatives which contain both an alkyl or substituted alkyl and a carboxyl containing substituent may be prepared by reacting the starting material with a limited quantity of one reagent so as to leave vacant some possible sites of substitution, and then reacting the product of this reaction with another reagent. The alkyl groups or substituted alkyl group may be attached to the chitin chain in a manner similar to that used to attach carboxyalkyl groups. Thus, chitin or a derivative with unsubstituted 6-hydroxyl groups may be reacted in an organic solvent, with an alkyl halide or substituted alkyl halide in order to form a derivative containing an alkyl group or substituted alkyl group attached to the 6-hydroxyl oxygen. Alkyl groups or substituted alkyl groups may be attached to the nitrogen by treating chitosan or a chitosan derivative with unsubstituted nitrogen with a dialkyl sulfate or an alkyl or substituted alkyl halide.

While derivatives with any ratio of alkyl or substituted alkyl substituents to carboxyl containing substituents may be prepared merely by adjusting the amounts of reagents used in the successive reactions, for the purposes of the present invention, the carboxyl containing substituents should be predominant. It is preferred to have between 5 and 30 percent alkyl or substituted alkyl substituents and the rest carboxyl containing substituents. Such derivatives are hygroscopic but not highly soluble in pure water and thus able to absorb water which may condense on windows without being dissolved. The presence of a preponderance of carboxyl groups, however, assures that the material is soluble in basic detergent solutions, and thus a film of the material is readily removable from a window.

For use in the present invention, the chitin derivatives are dissolved in a mixture of water soluble organic solvent and water and dispersed either in an aerosol form or in a spray composition. If only the defogging properties of the chitin derivative are desired, no fragrance need be added to the composition. Such a formulation would be useful on eyeglasses. It is possible, however, to utilize the fragrance retaining and absorbing properties of the chitin derivatives to prepare a material which will function as a deodorant by slowly releasing a fragrance, absorb unpleasant odors, while at the same time function as a defogger.

While it is desirable to have the finished product contain as much chitin derivative as possible, in order to assure that the product spread evenly on the surface to be treated, the amount of chitin in the composition must be limited to avoid excessive viscosity. Thus, a product which contains too much chitin, will be too viscous to be properly sprayed or expelled from an aerosol container, and too viscous to spread in an even invisible film on a surface. The preferred composition contains between 0.75 and 1.5 percent of an appropriate chitin derivative.

Of course, if the material is to be used only as a deodorant, the evenness and clarity of the film may not be important. In this case, the preferred composition may contain between 2 and 5 percent of the appropriate chitin derivative.

The following examples are provided for illustrative purposes and may include particular features of the invention. However, the examples should not be construed to limiting the invention, many variations of which are possible without departing from the spirit or scope thereof.

EXAMPLE 1

Preparation of Ethyl, Carboxymethyl Chitin

To 110 grams of chitin in 1000 grams of dimethyl sulfoxide is added 40 grams of sodium hydroxide. The mixture is stirred for about one half-hour. The mixture is warmed to 50° C. and 10 grams of ethyl bromide is added. The temperature is maintained at 50° C. and the stirring is continued for 4 hours, whereupon the mixture is cooled and filtered in order to remove dimethyl sulfoxide from the partially ethylated chitin. The partially reacted chitin is suspended in 1 liter of isopropyl alcohol containing 40 grams of sodium hydroxide and 50 grams of chloroacetic acid. The mixture is warmed to 50° C. and stirred, at this temperature, for a period of 2 hours. The alcohol insoluble chitin derivative is collected by filtration and washed with isopropyl alcohol.

EXAMPLE 2

A Window or Eyeglass Defogger

A solution of the following composition is prepared:

| | | Weight Percent |
|---|---|---|
| Chitin derivative of Example 1 | | 1.5 |
| Water | | 50 |

-continued

| | | Weight Percent |
|---|---|---|
| Alcohol | to | 100 |

When sprayed upon a surface, this material prevents fog formation.

EXAMPLE 3

A Window Defogger and Deodorizer

A solution of the following composition is prepared:

| | | Weight Percent |
|---|---|---|
| Chitin derivative of Example 1 | | 1.5 |
| Water | | 50 |
| Perfume | | 2 |
| Alcohol | to | 100 |

When sprayed upon a surface, this material will slowly release fragrance, and act as a defogger.

EXAMPLE 4

A Window or Eyeglass Defogger Using Carboxymethyl Chitin

A solution of the following composition is prepared:

| | | Weight Percent |
|---|---|---|
| Carboxymethyl chitin | | 1.5 |
| Water | | 50 |
| Alcohol | to | 100 |

What is claimed:

1. A method for reducing the formation of fog on a transparent surface by disposing upon said surface a thin film of a carboxyl containing chitin derivative 2. The method according to claim 1 in which the surface is glass.

3. The method according to claim 1 in which the surface is a transparent plastic material.

4. The method according to claim 1 in which the chitin derivative is selected from the group consisting of O-carboxyalkyl chitin, N-carboxyalkyl chitosans, and N-carboxyacyl chitosans.

5. The method according to claim 1 in which the chitin derivative is O-substituted chitin containing a major amount of carboxyalkyl substituents and a minor amount of substituents selected from the following group: alkyl, alkoxyalkyl or, carboalkoxyalkyl; or the chitin derivative is a N-substituted chitosan containing both carboxyalkyl substituents and substituents selected from the following group: alkyl, alkoxyalkyl, or carboalkoxyalkyl.

6. A method according to claim 1 in which said thin film of a carboxyl containing chitin derivative has disposed therein a perfume material.

* * * * *